(12) United States Patent
Fischer et al.

(10) Patent No.: US 12,589,203 B2
(45) Date of Patent: *Mar. 31, 2026

(54) SYSTEM AND METHOD FOR GENERATING BATTERY ALARMS IN INFUSION DEVICES

(71) Applicants: BAXTER INTERNATIONAL INC., Deerfield, IL (US); BAXTER HEALTHCARE SA, Glattpark (CH)

(72) Inventors: Steven Ward Fischer, Gurnee, IL (US); Matthew Stephen Vogel, Spring Grove, IL (US); Ye Chen, Lake Forest, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/779,744

(22) Filed: Jul. 22, 2024

(65) Prior Publication Data

US 2024/0374821 A1     Nov. 14, 2024

Related U.S. Application Data

(63) Continuation of application No. 17/566,090, filed on Dec. 30, 2021, now Pat. No. 12,042,628.

(Continued)

(51) Int. Cl.
G01R 31/367 (2019.01)
A61M 5/142 (2006.01)
(Continued)

(52) U.S. Cl.
CPC ......... *A61M 5/172* (2013.01); *G01R 31/3646* (2019.01); *G01R 31/367* (2019.01);
(Continued)

(58) Field of Classification Search
None
See application file for complete search history.

(56) References Cited

U.S. PATENT DOCUMENTS 5,764,064 A     6/1998 Bowman et al.
6,064,180 A *   5/2000 Sullivan ................. B60L 58/10
320/132

(Continued)

*Primary Examiner* — Curtis A Kuntz
*Assistant Examiner* — Jerold B Murphy
(74) *Attorney, Agent, or Firm* — K & L Gates LLP

(57) ABSTRACT

A system and method are disclosed for detecting remaining battery voltage or capacity in an infusion device and generating alarms based on the detection. A battery lifetime extension method includes providing an infusion device that derives its power from a rechargeable battery. The infusion device may derive its power from a rechargeable battery. Furthermore, the infusion device receives, at predetermined intervals of time in real-time sensor data comprising a voltage, a change in the voltage over the predetermined interval of time, an average current, a temperature, and a remaining voltage or capacity reported by a battery gas gauge integrated circuit ("IC") associated with the rechargeable battery. A customized neural network model utilizes the sensor data to determine an indicia of the actual remaining voltage or capacity of the rechargeable battery in real-time. The indicia may be used to lengthen and/or abate ongoing medical infusion therapy.

16 Claims, 7 Drawing Sheets

Related U.S. Application Data

(60) Provisional application No. 63/132,177, filed on Dec. 30, 2020.

(51) Int. Cl.
| | |
|---|---|
| *A61M 5/172* | (2006.01) |
| *G01R 31/36* | (2020.01) |
| *G01R 31/3842* | (2019.01) |
| *H01M 10/48* | (2006.01) |
| *H02J 7/00* | (2006.01) |
| *H04L 67/12* | (2022.01) |

(52) U.S. Cl.
CPC ...... *G01R 31/3842* (2019.01); *H01M 10/488* (2013.01); *H02J 7/00032* (2020.01); *H02J 7/0048* (2020.01); *H04L 67/12* (2013.01); *A61M 2205/18* (2013.01); *A61M 2205/3327* (2013.01); *A61M 2205/8206* (2013.01); *H01M 2220/30* (2013.01)

(56) References Cited

U.S. PATENT DOCUMENTS

| | | | | |
|---|---|---|---|---|
| 10,996,726 | B1 * | 5/2021 | Thompson | G06F 1/26 |
| 11,594,770 | B2 * | 2/2023 | Kuriki | G06N 3/04 |
| 12,042,628 | B2 * | 7/2024 | Fischer | G01R 31/3842 |
| 2006/0107148 | A1 * | 5/2006 | Ginggen | A61N 1/37276 |
| | | | | 714/733 |
| 2008/0167531 | A1 | 7/2008 | McDermott | |
| 2009/0069749 | A1 | 3/2009 | Miller et al. | |
| 2009/0273318 | A1 | 11/2009 | Rondoni et al. | |
| 2011/0130984 | A1 | 6/2011 | Schmidt et al. | |
| 2012/0235485 | A1 | 9/2012 | Trock et al. | |
| 2014/0374475 | A1 * | 12/2014 | Kallfelz | H01M 10/4285 |
| | | | | 235/375 |
| 2015/0196709 | A1 * | 7/2015 | Jacobson | A61M 5/142 |
| | | | | 604/67 |
| 2016/0299196 | A1 | 10/2016 | Labarthe et al. | |
| 2018/0026454 | A1 | 1/2018 | Belkacem-Boussaid et al. | |
| 2019/0157891 | A1 | 5/2019 | Chemali et al. | |
| 2020/0153264 | A1 | 5/2020 | Osada et al. | |

* cited by examiner

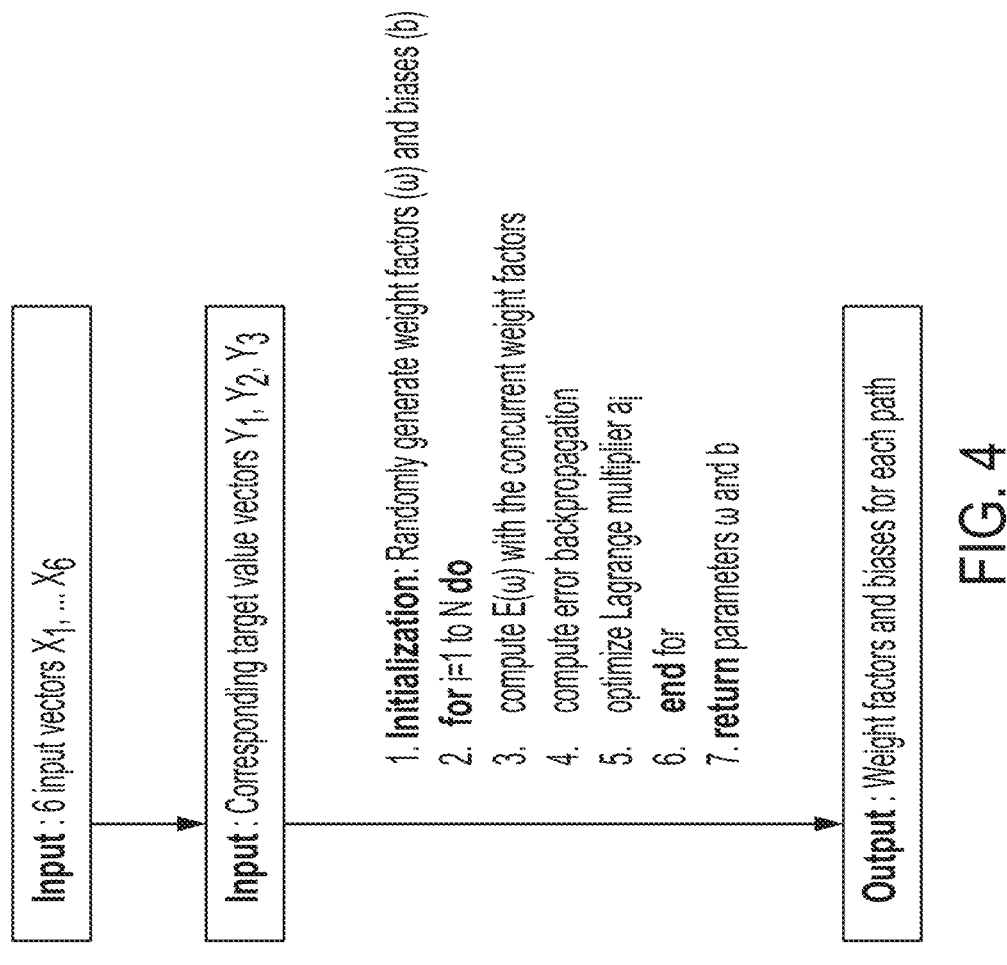

Input : 6 input vectors $X_1 ... X_6$

Input : Corresponding target value vectors $Y_1, Y_2, Y_3$

1. Initialization: Randomly generate weight factors ($\omega$) and biases (b)
2. for i=1 to N do
3.   compute E($\omega$) with the concurrent weight factors
4.   compute error backpropagation
5.   optimize Lagrange multiplier $a_i$
6. end for
7. return parameters $\omega$ and b

Output : Weight factors and biases for each path

FIG. 4

SYSTEM AND METHOD FOR GENERATING BATTERY ALARMS IN INFUSION DEVICES

PRIORITY CLAIM

This application claims priority to and the benefit as a continuation application of U.S. patent application Ser. No. 17/566,090, filed Dec. 30, 2021, now U.S. Pat. No. 12,042, 628, which is a non-provisional application of U.S. Provisional Patent Application No. 63/132,177, filed Dec. 30, 2020, the entire contents of which are hereby incorporated by reference and relied upon.

BACKGROUND

Generally, medical patients sometimes require precise intravenous ("IV") delivery of either continuous medication or medication at set periodic intervals using infusion pumps. Known infusion pumps provide controlled fluid medication or drug infusion where the fluid can be administered at a precise rate that keeps a medication/drug concentration within a therapeutic margin and out of an unnecessary or possibly toxic range. The infusion pumps provide appropriate medication/drug delivery to a patient at a controllable rate, which does not require frequent attention.

Infusion pumps may facilitate administration of intravenous therapy to patients both in and outside of a clinical setting. Outside a clinical setting, doctors have found that in many instances patients can return to substantially normal lives, provided that they receive periodic or continuous intravenous administration of medication, drugs, or other fluids such as saline. Among the types of therapies requiring this kind of administration are antibiotic therapy, chemotherapy, pain control therapy, nutritional therapy, and several other types that are known by those skilled in the art. In many cases, patients receive multiple daily therapies. Certain medical conditions require infusion of drugs in a solution over relatively short periods such as from thirty minutes to two hours. These conditions and others have collectively promoted the development of increasingly lightweight, portable or ambulatory infusion pumps that can be worn by a patient and are capable of administering a continuous supply of medication at a desired rate, or providing several doses of medication at scheduled intervals.

Known infusion pumps include elastomeric pumps, which squeeze solution from flexible containers, such as balloons, into IV tubing for delivery to a patient. Alternatively, infusion pumps may include spring-loaded pumps that pressurize solution containers or reservoirs. Certain pump designs utilize cartridges containing flexible compartments that are squeezed by pressure rollers for discharging the solutions. Further, known infusion pumps include peristaltic pumps having finger actuators or a roller actuator that apply pressure to IV tubing for delivering fluid from a fluid container to a patient.

Infusion pumps utilizing syringes are also known. These syringe pumps use a drive mechanism to move a plunger of a syringe to deliver a fluid to a patient. Typically, these infusion pumps include a housing adapted to receive a syringe assembly, a drive mechanism adapted to move the syringe plunger, and a pump control unit having a variety of operating controls.

Most known infusion systems use a rechargeable battery to provide power when the system is not plugged into AC power. These rechargeable batteries typically include "smart" batteries, as they include a battery gas gauge integrated circuit ("IC"). The battery gas gauge IC provides data regarding a current status of the battery, including its remaining voltage or capacity. The battery gas gauge IC can also measure a battery cell voltage, a temperature, and a current to determine the remaining voltage or capacity of the battery, e.g., by determining a total charge going into and coming out of the battery, and by determining an internal impedance of the battery. The calculated impedance of the battery can be compared to battery impedance profiles stored in the battery gas gauge IC to estimate the remaining voltage or capacity of the battery. However, this estimated remaining voltage or capacity can often be erroneous, due to factors that are not known to the battery gas gauge IC.

Furthermore, the power management software of the infusion system may use this erroneous remaining voltage or capacity, reported by the battery gas gauge IC, to calculate the remaining runtime of the infusion system ("run-time remaining"), which is the amount of time the infusion system can continue to deliver medication to the patient until the battery is fully depleted. The run-time remaining value can be used to determine when "low", "very low", and "depleted" battery alarms should be issued. However, since the remaining voltage or capacity value reported by the battery gas gauge IC can be inherently inaccurate, the run-time remaining value may also be inaccurate. This leads to situations where battery alarms indicating low levels of battery voltage or capacity are issued at incorrect times, leading to situations where the infusion pump cannot run for as long as needed after battery alarms are issued. This can lead to undesirable clinical outcomes, such as an unexpected interruption of an infusion therapy.

To compensate for these shortcomings, a margin of time is often added to the calculated run-time remaining value in order to ensure that the infusion system can run for a desired length of time. However, in more typical situations, this added margin can often result in shutting down the system even when there may still be remaining voltage or capacity left in the battery.

Accordingly, a more reliable and accurate method and system for detecting and issuing alarms based on remaining battery voltage or capacity is desired.

SUMMARY

The present disclosure provides a new and innovative method and system for detecting remaining battery voltage or capacity and generating alarms based on the detection. In various embodiments, the device utilizing the disclosed method and system for the detection and the alarming of remaining battery voltage or capacity is an infusion pump. The infusion pump may comprise a peristaltic pump, a syringe pump, or an ambulatory pump configured to deliver a medication to a patient. It should be appreciated that the device is in various embodiments, any type of medical device, or any other suitable device having a rechargeable battery.

The disclosed method includes using software run by an infusion device to monitor the remaining battery voltage or capacity and generate alarms if the remaining battery voltage or capacity falls below predetermined thresholds (e.g., if the remaining battery voltage or capacity indicates "low battery," "very low battery," or a "depleted battery"). The software may comprise instructions stored in a memory of the infusion device, and may be executable by one or more processors of the infusion device. Furthermore, the infusion device may derive its power from a rechargeable battery, and may receive various data from the rechargeable battery e.g., via sensors. In one embodiment, the infusion device may receive in real-time, at predetermined intervals of time, measurements including a voltage of the rechargeable battery, a change in the voltage over the predetermined interval of time, an average current associated with the rechargeable battery, a temperature of the rechargeable battery, and/or a remaining voltage or capacity reported by a battery gas gauge integrated circuit ("IC") associated with the rechargeable battery. The received measurements may be used to generate a feature vector.

The method may further comprise deploying the feature vector into a neural network previously trained to determine an actual remaining voltage or capacity of the rechargeable battery. The trained neural network may comprise weight factors and biases calculated for a plurality of paths through a plurality of layers (e.g., an input layer, a plurality of hidden layers, and an output layer). Furthermore, the neural network may be trained from a training dataset comprising the above measurements from reference data (e.g., the above measurements from other rechargeable batteries) with known and actual remaining capacities. After deployment of the feature vector into the trained neural network, the infusion device is configured to determine an indicia of the actual remaining voltage or capacity of the rechargeable battery in real-time based on the measurements it received at a given interval of time. In some aspects, the indicia of the actual remaining voltage or capacity may indicate whether the actual remaining voltage or capacity satisfies a predetermined threshold for a low battery voltage or capacity, a very low battery voltage or capacity, and/or a depleted battery voltage or capacity. The infusion device may generate an alarm if one or more of these thresholds are met.

It has been shown that determining remaining battery voltage or capacity through the artificial neural network, and generating alarms based accordingly, is significantly more accurate and reliable than conventional methods. Thus, the systems and methods disclosed herein reduce the time and effort spent towards mitigating the effect of inaccurate or erroneous indications of remaining battery voltage or capacity found using conventional methods. An additional benefit of the disclosed method includes an improvement to medical care of the patient, as there will be less interruptions in infusion therapy as a result of unreliable indications of battery depletion.

In light of the disclosure herein and without limiting the disclosure in any way, in a first aspect of the present disclosure, which may be combined with any other aspect listed herein unless specified otherwise, an infusion device includes a rechargeable battery having a gas gauge integrated circuit ("IC"), one or more processors, and memory storing instructions that, when executed by the one or more processors, cause the one or more processors to receive, at predetermined intervals of time in real-time, measurements comprising a voltage of the rechargeable battery, a change in the voltage over the predetermined interval of time, an average current associated with the rechargeable battery, a temperature of the rechargeable battery, and a remaining voltage or capacity reported by the gas gauge IC. The one or more processors are also configured to generate a feature vector comprising the voltage, the change in the voltage, the average current, the temperature, the remaining voltage or capacity reported by the gas gauge IC, and a full charge voltage or capacity of the rechargeable battery and apply the feature vector to a trained neural network to determine an actual remaining voltage or capacity of the rechargeable battery. The trained neural network comprises weight factors and biases for calculating a plurality of paths through a plurality of layers. The one or more processors are further configured to generate, in real-time, an alarm indicating that the actual remaining voltage or capacity of the rechargeable battery is below a predetermined threshold when the actual remaining voltage or capacity of the rechargeable battery is below the predetermined threshold.

In accordance with a second aspect of the present disclosure, which may be used in combination with any other aspect listed herein unless stated otherwise, the predetermined threshold includes a first threshold corresponding to a low battery state, a second threshold corresponding to a very low battery state, and a third threshold corresponding to a depleted battery state.

In accordance with a third aspect of the present disclosure, which may be used in combination with any other aspect listed herein unless stated otherwise, the trained neural network is configured to use the feature vector to determine if any of the first, second, or third thresholds are satisfied, when the first threshold is reached and the second threshold is not reached, indicate the low battery state for the alarm, when the first and second thresholds are reached and the third threshold is not reached, indicate the very low battery state for the alarm, and when the first, second, and third thresholds are reached, indicate the depleted battery state for the alarm.

In accordance with a fourth aspect of the present disclosure, which may be used in combination with any other aspect listed herein unless stated otherwise, the low battery state corresponds to 30 minutes before the depleted battery state is reached and the very low battery state corresponds to 15 minutes before the depleted battery state is reached.

In accordance with a fifth aspect of the present disclosure, which may be used in combination with any other aspect listed herein unless stated otherwise, the depleted battery state corresponds to three to four minutes before the rechargeable battery is depleted and can no longer provide power.

In accordance with a sixth aspect of the present disclosure, which may be used in combination with any other aspect listed herein unless stated otherwise, the one or more processors are configured to generate feature vectors and apply the feature vectors in real-time to the trained neural network at periodic intervals including at least one of every 50 milliseconds, 100 milliseconds, 500 milliseconds, 1 second, 2 seconds, 5 seconds, 30 seconds, or 1 minute.

In accordance with a seventh aspect of the present disclosure, which may be used in combination with any other aspect listed herein unless stated otherwise, the one or more processors are configured to transmit the alarm to a server via a network.

In accordance with an eighth aspect of the present disclosure, which may be used in combination with any other aspect listed herein unless stated otherwise, the one or more processors are configured to display an indication of the alarm on a user interface.

In accordance with a ninth aspect of the present disclosure, which may be used in combination with any other aspect listed herein unless stated otherwise, an infusion device includes a rechargeable battery having a gas gauge integrated circuit ("IC"), a user interface, a battery sensor, one or more processors, and memory storing a plurality of trained neural networks for different rechargeable battery types and instructions that, when executed by the one or more processors, cause the one or more processors to receive from the gas gauge IC information indicative of a type of the rechargeable and select one of the trained neural networks based on the information from the gas gauge IC. The one or more processors are also configured to at least one of receive or determine, at predetermined intervals of time in real-time, measurements comprising a voltage of the rechargeable battery from the battery sensor, a change in the voltage over the predetermined interval of time, an average current associated with the rechargeable battery from the battery sensor, a temperature of the rechargeable battery from the battery sensor, and a remaining voltage or capacity reported by the gas gauge IC. The one or more processors are further configured to generate a feature vector comprising the voltage, the change in the voltage, the average current, the temperature, the remaining voltage or capacity reported by the gas gauge IC, and a full charge voltage or capacity of the rechargeable battery and apply the feature vector to the selected trained neural network to determine an actual remaining voltage or capacity of the rechargeable battery. The trained neural network comprises weight factors and biases for calculating a plurality of paths through a plurality of layers. The one or more processors are additionally configured to generate, in real-time, an alarm indicating that the actual remaining voltage or capacity of the rechargeable battery is below a predetermined threshold when the actual remaining voltage or capacity of the rechargeable battery is below the predetermined threshold.

In accordance with a tenth aspect of the present disclosure, which may be used in combination with any other aspect listed herein unless stated otherwise, the predetermined threshold includes a first threshold corresponding to a low battery state, a second threshold corresponding to a very low battery state, and a third threshold corresponding to a depleted battery state.

In accordance with an eleventh aspect of the present disclosure, which may be used in combination with any other aspect listed herein unless stated otherwise, the trained neural network is configured to use the feature vector to determine if any of the first, second, or third thresholds are satisfied, when the first threshold is reached and the second threshold is not reached, indicate the low battery state for the alarm, when the first and second thresholds are reached and the third threshold is not reached, indicate the very low battery state for the alarm, and when the first, second, and third thresholds are reached, indicate the depleted battery state for the alarm.

In accordance with a twelfth aspect of the present disclosure, which may be used in combination with any other aspect listed herein unless stated otherwise, the one or more processors are configured to transmit the alarm to a server via a network.

In accordance with a thirteenth aspect of the present disclosure, which may be used in combination with any other aspect listed herein unless stated otherwise, the one or more processors are configured to display an indication of the alarm on the user interface.

In accordance with a fourteenth aspect of the present disclosure, which may be used in combination with any other aspect listed herein unless stated otherwise, an infusion system includes a server configured to generate a plurality of trained neural networks and an infusion device communicatively coupled to the server via a network. The infusion device includes a rechargeable battery having a gas gauge integrated circuit ("IC"), one or more processors, and memory storing instructions that, when executed by the one or more processors, cause the one or more processors to receive at least one trained neural network from the server. The received trained neural network comprises weight factors and biases for calculating a plurality of paths through a plurality of layers. The one or more processors are also configured to receive, at predetermined intervals of time in real-time, measurements comprising a voltage of the rechargeable battery, a change in the voltage over the predetermined interval of time, an average current associated with the rechargeable battery, a temperature of the rechargeable battery, and a remaining voltage or capacity reported by the gas gauge IC. The one or more processors are further configured to generate a feature vector comprising the voltage, the change in the voltage, the average current, the temperature, the remaining voltage or capacity reported by the gas gauge IC, and a full charge voltage or capacity of the rechargeable battery, apply the feature vector to the received trained neural network to determine an actual remaining voltage or capacity of the rechargeable battery, and generate, in real-time, an alarm indicating that the actual remaining voltage or capacity of the rechargeable battery is below a predetermined threshold when the actual remaining voltage or capacity of the rechargeable battery is below the predetermined threshold.

In accordance with a fifteenth aspect of the present disclosure, which may be used in combination with any other aspect listed herein unless stated otherwise, the server is configured to generate the plurality of trained neural networks for different rechargeable battery types, receive an indication of a rechargeable battery type of the infusion device, select a trained neural network that corresponds to the rechargeable battery type at the infusion device, and transmit the selected trained neural network to the infusion device.

In accordance with a sixteenth aspect of the present disclosure, which may be used in combination with any other aspect listed herein unless stated otherwise, the server is configured to, for each rechargeable battery type, generate, for each of a plurality of reference data obtained during discharging of reference batteries, a reference feature vector comprising a reference voltage of a reference battery, a change in the reference voltage over a predetermined interval of time, a reference average current associated with the reference battery, a reference temperature associated with the reference battery, and a reference remaining voltage or capacity reported by a battery gas gauge integrated circuit ("IC") associated with the reference battery. The server is also configured to, for each rechargeable battery type, associate, for each of the plurality of reference data, the reference feature vector with a corresponding output vector indicating an actual reference remaining voltage or capacity and train, using the associated reference feature vectors, one of the neural networks to determine the actual remaining voltage or capacity of the rechargeable battery type.

In accordance with a seventeenth aspect of the present disclosure, which may be used in combination with any other aspect listed herein unless stated otherwise, the predetermined threshold includes a first threshold corresponding to a low battery state, a second threshold corresponding to a very low battery state, and a third threshold corresponding to a depleted battery state.

In accordance with an eighteenth aspect of the present disclosure, which may be used in combination with any other aspect listed herein unless stated otherwise, the received trained neural network is configured to use the feature vector to determine if any of the first, second, or third thresholds are satisfied, when the first threshold is reached and the second threshold is not reached, indicate the low battery state for the alarm, when the first and second thresholds are reached and the third threshold is not reached, indicate the very low battery state for the alarm, and when the first, second, and third thresholds are reached, indicate the depleted battery state for the alarm.

In accordance with a nineteenth aspect of the present disclosure, which may be used in combination with any other aspect listed herein unless stated otherwise, the one or more processors are configured to transmit the alarm to a server via the network.

In accordance with a twentieth aspect of the present disclosure, which may be used in combination with any other aspect listed herein unless stated otherwise, the one or more processors are configured to display an indication of the alarm on the user interface.

In accordance with a twenty-first aspect of the present disclosure, any of the structure, functionality, and alternatives disclosed in connection with any one or more of FIGS. 1 to 7 may be combined with any other structure, functionality, and alternatives disclosed in connection with any other one or more of FIGS. 1 to 7.

In light of the present disclosure and the above aspects, it is therefore an advantage of the present disclosure to provide an infusion system configured to use a trained neural network to determine when a battery reaches a low state, a very low state, and a depletion state.

It is another advantage of the present disclosure to use a trained neural network to overcome inaccuracies of using a battery's internal gas gauge to measure remaining battery voltage or capacity.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE DRAWINGS

FIG. 4 is a flow chart illustrating an example method for training a neural network for detecting, and generating alarms for, remaining battery voltage, according an embodiment of the present disclosure.

DETAILED DESCRIPTION

Monitoring remaining battery voltage and generating alarms for low remaining battery voltage levels or capacity for providing a charge are critical safety measures for medication delivery infusion systems. Low remaining battery voltage levels may include "low," "very low," and "depleted" remaining battery voltage levels, each of which may trigger an alarm if detected. For each alarm, there may be a specified remaining time for infusion by United States Food and Drug Administration ("FDA") regulations and manufacturer requirements. However, since batteries may vary as a result of different initial conditions and discharging characteristics, false alarms are often observed, e.g., due to false measurements of remaining battery capacities.

Disclosed herein are novel and nonobvious systems and methods for battery alarms and remaining battery voltage detection using neural network models, which significantly improve known battery alarm and remaining battery voltage detection systems, and make infusion devices safer for patients. The disclosed method combines the benefits of a more accurate and reliable reporting of battery voltage while reducing or eliminating time and labor typically spent to calibrate faulty indications of remaining battery voltage. The disclosed method also improves patient care as a result of less interruptions during an infusion therapy.

Figure 1:
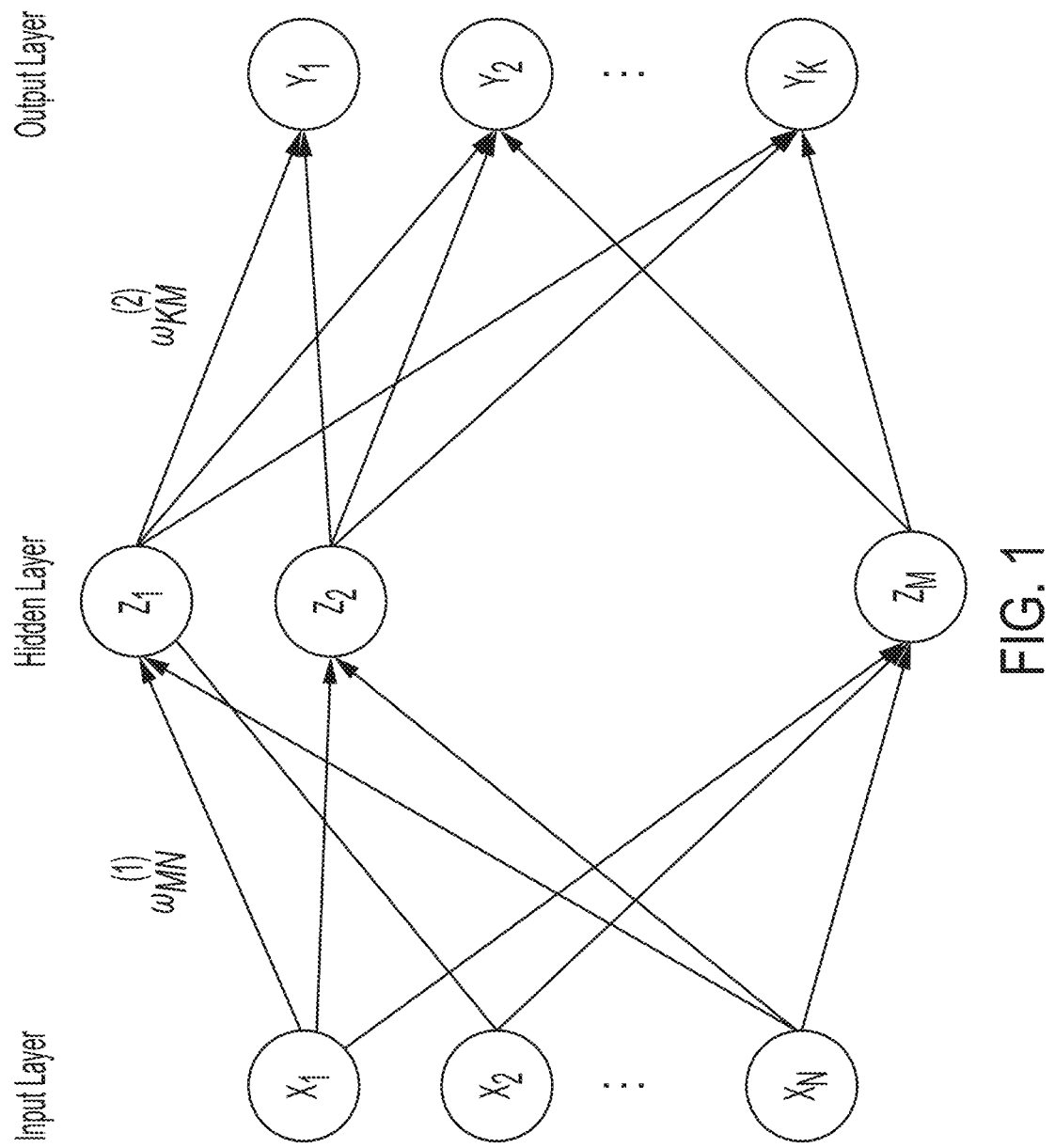
FIG. 1 is a flow chart illustrating an example artificial neural network, according to an embodiment of the present disclosure.

FIG. 1 is a flow diagram illustrating an example artificial neural network, in accordance with an exemplary embodiment of the present disclosure. The artificial neural network, which is utilized in the present disclosure, includes an input layer, one or more hidden layers, and an output layer. The input layer may include nodes (e.g., X1, X2, . . . XN) corresponding to a plurality of battery parameters. In one embodiment, six battery parameters may be used, which may result in a neural network structure having six input nodes. Each hidden layer may include a plurality of nodes for optimization (e.g., Z1, Z2 . . . ZM). The optimization may occur by way of forward propagation, back propagation, and a calibration of weights and biases. In one embodiment, the neural network may include a single hidden layer comprising eight nodes for optimization. The output layer may generate one or more output parameters (e.g., Y1, Y2, . . . YK). In one embodiment, the neural network model may include three output nodes to correspond to three respective output parameters, representing indications of "low," "very low," and "depleted" remaining battery capacities. Since the input data from a battery may be continuous and accumulated, the three sets of output data can be consolidated into one neural network model.

While input data may be supplied at the input layer, each node may receive a combination of one or more input variables, e.g., from nodes of the preceding layer. For example, the combination of inputs, $a_j$, for the $j^{th}$ node in the hidden layer can be expressed as the following equation:

$$a_j = \sum_{i=1}^{N} \omega_{ji}^{(1)} x_i + b_j^{(1)},$$

where j=1, . . . , M, the superscript (1) indicates that the corresponding parameter is in the first layer of the network, the parameters $$\omega_{ji}^{(1)}$$

are weights, and the parameters $$b_j^{(1)}$$

are biases. A nonlinear activation function h(.) can provide an output ($Z_j$) of each node of the hidden layer, which can be expressed as:

$$Z_j = h(a_j)$$

A sigmoid function can be used as the activation function, which can be expressed as:

$$h(a) = \frac{1}{1 + \exp(-a)}$$

Furthermore, the layers may be combined to find the overall neural network function:

$$y_K(x, \omega, b) = h\left(\sum_{j=1}^{M} \omega_{kj}^{(2)} h\left(\sum_{i=1}^{N} \omega_{ji}^{(1)} x_i + b_j^{(1)}\right) + b_k^{(2)}\right),$$

Hence, the neural network model may comprise a nonlinear function from a set of input variables $\{x_i\}$ to a set of output variables $\{y_k\}$. In one embodiment, there are seven input variables and three output variables. There may be as few as two input variables and as many as twelve input variables.

Given a training set comprising a set of input vectors $\{x_i\}$, where n=1, . . . , N, together with a corresponding set of target vectors $\{t_n\}$, training a neural network may involve minimizing the error function, also called a loss function, by a mean square error ("MSE") method. For the first iteration of computations through the nodes of each of the layers of the neural network (e.g., from the input layer to the output layer), initial weight factors and biases are randomly selected and/or initialized. Then, through feed-forward calculations, the loss can be calculated using the following formula:

$$E(\omega) = 1/2 \sum_{n=1}^{K} \|y(x_n, \omega) - t_n\|^2$$

If the loss is larger than a predefined tolerance, the weight factors can be revised before the next iteration starts. The neural network model may be considered trained when the predefined tolerance has been achieved (e.g., the loss is lower than the predefined tolerance).

To improve computational efficiency, an error backpropagation method can be utilized. For example, optimization of the parameter, $$\omega_{ji}^{(1)}$$

in FIG. 1 can be achieved via the expression:

$$\frac{\partial E}{\partial \omega_{MN}^{(1)}} = \frac{\partial E}{\partial y_K} * \frac{\partial y_K}{\partial Z_M} * \frac{\partial Z_M}{\partial \omega_{MN}^{(1)}}$$

Furthermore, the revised $$\omega_{ji}^{(1)}$$

can be achieved by using stochastic gradient descent optimization, using the following expression:

$$\omega_{ji}^{(1)+} = \omega_{ji}^{(1)} + \eta \frac{\partial E}{\partial \omega_{ji}^{(1)}}$$

where η is the learning step size, and $$\omega_{ji}^{(1)+}$$

is the updated weight factor. The above described method for optimizing a given parameter, $$\omega_{ji}^{(1)}$$

can be applied for all parameters in order to perform the next iteration.

In some embodiments, the number of back-propagation iterations for a neural network model to detect and generate alarms for remaining battery voltage is approximately 5000 iterations. In some embodiments, the number of iterations is limited to 5000 to prevent a situation of "over-training" the model where the model becomes overly tuned to the specific training data set.

In one embodiment, the following features may be used to obtain and build input data for the neural network model: a time stamp (e.g., for further calculations); a measurement of a voltage (e.g., to be used directly as an input value for the neural network model); a measurement of current (e.g., for further filtering of the input data); a measurement of temperature (e.g., to be used directly as an input value for the neural network model); a measurement of an average current (e.g., to be used directly as an input value for the neural network model); a remaining voltage (e.g., to be used directly as an input value for the neural network model); and a full charge voltage of the battery (e.g., to be used directly as an input value for the neural network model, for example, to indicate a battery state of health, and/or to provide an indication of battery age).

The sample time stamp may be used along with the voltage to create a measurement of a change in voltage over an interval of time (e.g., "delta milli-volts per second"), which can be used directly as an input value for the neural network model. The change in voltage may be used to provide the neural network model with a sense of rate of change over time.

The "current" feature may be used to determine when a rechargeable battery switched from a charging mode to a discharging mode. Understanding this switch may be important to build the neural network model, as it primarily involves the discharging portion of the cycle.

After filtering out the charging mode samples from the data set, the "remaining voltage" feature can be used to find the point where the battery is depleted (e.g., where the "remaining voltage or capacity" is zero or near zero). From this point, additional training fields can be added to denote when the low battery, very low battery, and depleted battery alarms should occur. Since these samples were taken on a 2-minute cycle, some adjustments can be made to further improve the timing of the alarms.

In one embodiment, the alarm indicating a "depleted battery" may be issued 4 minutes from the zero "remaining voltage point. The alarm indicating "very low battery" may start 14 minutes from the alarm for "depleted battery." The alarm indicating "low battery" may start 30 minutes before the alarm for "depleted battery."

Given the above, the final preprocessed training data may include, but is not limited to, the following fields: a voltage; a change in voltage over an interval of time (e.g., delta milli-volts per second); an average current; a temperature; a remaining voltage; a full charge voltage (e.g., a battery state of health); a "low battery" alarm indication; a "very low battery" alarm indication; and a "depleted battery" alarm indication. The first six fields represent features for corresponding input values in FIG. 2, and the final three fields represent features for the output values shown in FIG. 3, as described further below.

Figure 2:
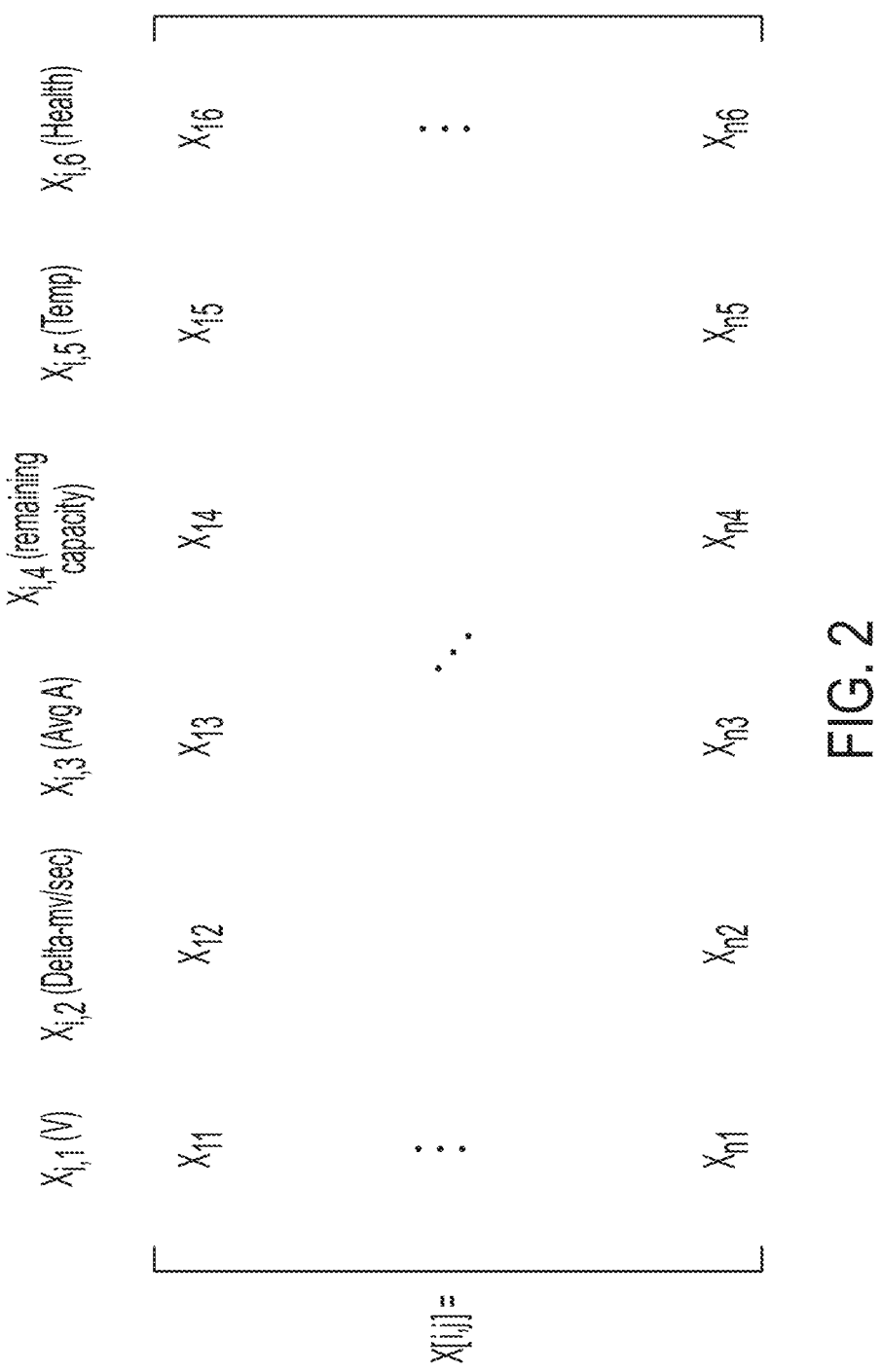
FIG. 2 is a diagram illustrating an input data matrix for using an artificial neural network for detecting, and generating alarms based on, remaining battery voltage, according to an embodiment of the present disclosure.

FIG. 2 is a diagram illustrating an input data matrix for using an artificial neural network for detecting and generating alarms based on remaining battery voltage, according to an embodiment of the present disclosure. As shown in FIG. 2, the six columns represent six features for input data that can be captured periodically from an infusion pump, e.g., in real-time. As shown in FIG. 2, X[i,j] represents input vectors including voltage, a change or difference in voltage over intervals of time (e.g., every second), an average current, a remaining battery voltage (e.g., as calculated by a battery gas gauge IC), a battery temperature, and a full charge voltage (battery state of health). The input data for these features may be sampled (e.g., received via sensors) at predetermined time intervals (e.g., every two minutes).

Figure 3:
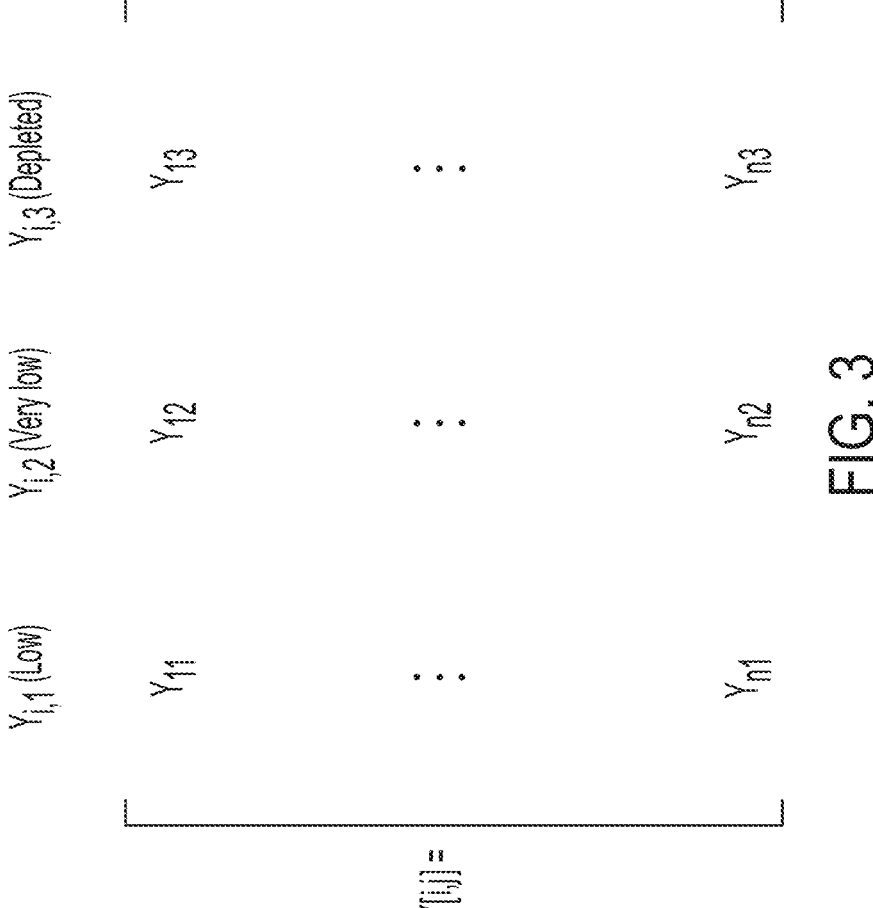
FIG. 3 is a diagram showing corresponding target vectors for the input data matrix of FIG. 2, according to an embodiment of the present disclosure.

FIG. 3 is a diagram showing the corresponding target vectors for the input data matrix of FIG. 2, according to an embodiment of the present disclosure. As shown in FIG. 3, Y[i,j] represents all target vectors including low, very low, and depleted battery status. In one embodiment, Y[i,j] may equal zero when the respective status is false, but Y[i,j] may equal one when the respective status is true.

FIG. 4 is a flow chart illustrating an example method for training a neural network for detecting and generating alarms for remaining battery voltage, according an embodiment of the present disclosure. In an example method of training the neural network, a reference feature vector may be received for each of a plurality of reference training data. The reference training data may be obtained during discharging of one or more reference batteries. Additionally or alternatively, the reference training data set may be a subset (e.g., half) of the test data set. Each reference feature vector may comprise a predetermined number of inputs, for example, a reference voltage of a reference battery; a change in the reference voltage over a predetermined interval of time; a reference average current associated with the reference battery; a reference temperature associated with the reference battery; and a reference remaining voltage reported by a battery gas gauge integrated circuit ("IC") associated with the reference battery. In other embodiments, fewer inputs or additional inputs may be used.

In the example shown in FIG. 4, each received reference vector may comprise six inputs. Furthermore, the training method may include inputting the corresponding target value vectors ("output vectors") for the reference feature vectors. As previously discussed, each target value vector may provide an indicia of the remaining battery voltage for the corresponding input data. For example, the target value may indicate whether the remaining battery voltage meets the thresholds for a "low battery," "very low battery," or a "depleted battery" indication. The reference feature vectors may be associated with their corresponding output vectors. The neural network model may be trained using the associated reference feature vectors to output weight factors and biases for each path of the neural network model. The training may include an iterative process comprising a feed forward propagation through the layers of the neural network model, a calculation of a loss function, and a back-propagation through the layers of the neural network model. However, at the first iteration, the training method may initialize by randomly generating weights and biases. After errors are minimized (e.g., the loss is within a tolerance level), the training method may return weight factors and biases for each path. These weight factors and biases associated with the trained neural network may be stored, e.g., for use in applying the trained neural network as shown in FIG. 5.

Figure 5:
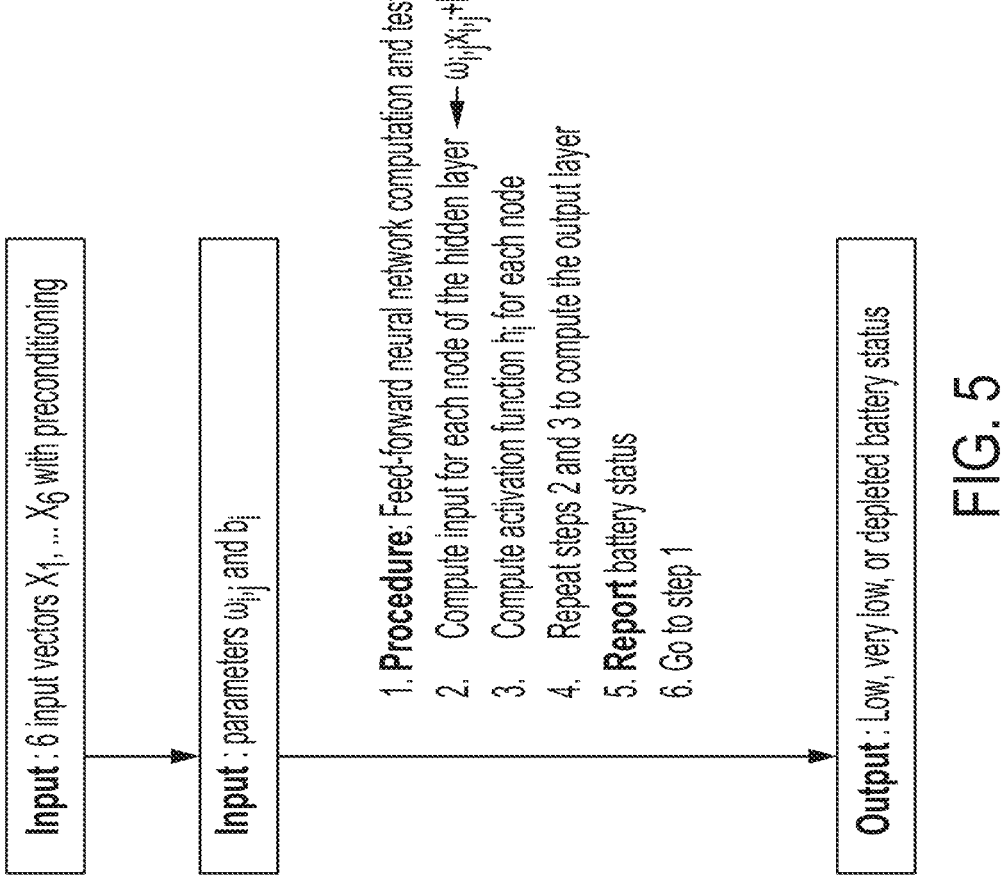
FIG. 5 is a flow chart illustrating an example method for applying a trained neural network for detecting, and generating alarms for, remaining battery voltage, according an embodiment of the present disclosure.

FIG. 5 is a flow chart illustrating an example method for applying a trained neural network for detecting and generating alarms for remaining battery voltage, according an embodiment of the present disclosure. Specifically, FIG. 5 illustrates a feed-forward computation using real-time battery data. For example, an infusion device being powered by a rechargeable battery may receive, at predetermined intervals of time in real-time, measurements comprising: a voltage of the rechargeable battery, a change in the voltage over the predetermined interval of time, an average current associated with the rechargeable battery, a temperature of the rechargeable battery, and a remaining voltage or capacity reported by a battery gas gauge integrated circuit ("IC"). The six types of input data may be used to form input feature vectors with preconditioning. The infusion device may also identify and retrieve the stored weight factors and biases from the training method of FIG. 4 (e.g., parameters $\omega_{ji}$ and $b_j$). The six-feature input vectors and stored weight factors and biases may be inputted into a neural network to generate an indicia of actual remaining voltage or capacity of the rechargeable battery (e.g., whether the rechargeable battery has "low battery," "very low battery," or "depleted battery" status). The application of the neural network model may involve performing feed-forward computations, computing inputs at each node of the hidden layer, and computing activation functions at each node.

In some embodiments, an infusion device selects a trained neural network and corresponding weight factors/biases parameters $\omega_{ji}$ and $b_j$ based on a known type of battery. In these instances, the battery gas gauge IC may transmit an identifier of a type of battery, which may specify a model number, manufacturer, version, etc. The infusion device uses the battery information from the battery gas gauge IC to select the corresponding rained neural network and corresponding weight factors/biases parameters $\omega_{ji}$ and $b_j$, which may be stored locally or remotely at a server.

As previously discussed, systems and methods of the present disclosure help to overcome the inaccuracies of using the battery's internal gas gauge IC to measure remaining battery voltage or capacity and generate alerts. Conventionally, these inaccuracies made it necessary to add a margin to the calculated run-time remaining value so that the battery could be guaranteed to have enough energy to allow an infusion to continue for the required amount of time after a low or very low battery alarm was issued. A desired outcome of using the neural network model discussed in the present disclosure is to reduce or eliminate the need for this margin. The disclosed methods for detecting and generating alarms for remaining battery voltage or capacity enables the infusion system to run for a longer period of time on battery power. To examine this possibility, the existing cache of battery alarm time data was analyzed as shown in the below table below time at which those alarms should be issued. For example, the previous known algorithm issues the low battery alarm when the battery is 78 minutes from empty. In the ideal case, the low battery alarm would be issued when the battery's time until empty is equal to 33 minutes (30 minutes of infusion run-time, plus an additional 3 minutes when the infusion system is alarming before it shuts down com-

| Remaining battery voltage/capacity (Wh) | Time until battery empty (minutes) | Ideal Method | | | Conventional Method | | |
|---|---|---|---|---|---|---|---|
| | | 30 minute alarm | 15 minute alarm | Depleted alarm | 30 minute alarm | 15 minute alarm | Depleted alarm |
| 9.9 | 86 | 0 | 0 | 0 | 0 | 0 | 0 |
| 9.7 | 84 | 0 | 0 | 0 | 0 | 0 | 0 |
| 9.5 | 82 | 0 | 0 | 0 | 0 | 0 | 0 |
| 9.3 | 80 | 0 | 0 | 0 | 0 | 0 | 0 |
| 9.1 | 78 | 0 | 0 | 0 | 1 | 0 | 0 |
| 8.8 | 76 | 0 | 0 | 0 | 1 | 0 | 0 |
| 8.6 | 74 | 0 | 0 | 0 | 1 | 0 | 0 |
| 8.4 | 72 | 0 | 0 | 0 | 1 | 0 | 0 |
| 8.2 | 70 | 0 | 0 | 0 | 1 | 0 | 0 |
| 7.9 | 68 | 0 | 0 | 0 | 1 | 0 | 0 |
| 7.7 | 66 | 0 | 0 | 0 | 1 | 0 | 0 |
| 7.5 | 64 | 0 | 0 | 0 | 1 | 0 | 0 |
| 7.3 | 62 | 0 | 0 | 0 | 1 | 0 | 0 |
| 7.0 | 60 | 0 | 0 | 0 | 1 | 1 | 0 |
| 6.8 | 58 | 0 | 0 | 0 | 1 | 1 | 0 |
| 6.6 | 56 | 0 | 0 | 0 | 1 | 1 | 0 |
| 6.3 | 54 | 0 | 0 | 0 | 1 | 1 | 0 |
| 6.1 | 52 | 0 | 0 | 0 | 1 | 1 | 0 |
| 5.9 | 50 | 0 | 0 | 0 | 1 | 1 | 0 |
| 5.6 | 48 | 0 | 0 | 0 | 1 | 1 | 0 |
| 5.4 | 46 | 0 | 0 | 0 | 1 | 1 | 0 |
| 5.2 | 44 | 0 | 0 | 0 | 1 | 1 | 1 |
| 4.9 | 42 | 0 | 0 | 0 | 1 | 1 | 1 |
| 4.7 | 40 | 0 | 0 | 0 | 1 | 1 | 1 |
| 4.5 | 38 | 0 | 0 | 0 | 1 | 1 | 1 |
| 4.2 | 36 | 0 | 0 | 0 | 1 | 1 | 1 |
| 4.0 | 34 | 1 | 0 | 0 | 1 | 1 | 1 |
| 3.8 | 32 | 1 | 0 | 0 | 1 | 1 | 1 |
| 3.5 | 30 | 1 | 0 | 0 | 1 | 1 | 1 |
| 3.3 | 28 | 1 | 0 | 0 | 1 | 1 | 1 |
| 3.1 | 26 | 1 | 0 | 0 | 1 | 1 | 1 |
| 2.8 | 24 | 1 | 0 | 0 | 1 | 1 | 1 |
| 2.6 | 22 | 1 | 0 | 0 | 1 | 1 | 1 |
| 2.4 | 20 | 1 | 0 | 0 | 1 | 1 | 1 |
| 2.1 | 18 | 1 | 1 | 0 | 1 | 1 | 1 |
| 1.9 | 16 | 1 | 1 | 0 | 1 | 1 | 1 |
| 1.6 | 14 | 1 | 1 | 0 | 1 | 1 | 1 |
| 1.4 | 12 | 1 | 1 | 0 | 1 | 1 | 1 |
| 1.2 | 10 | 1 | 1 | 0 | 1 | 1 | 1 |
| 0.9 | 8 | 1 | 1 | 0 | 1 | 1 | 1 |
| 0.6 | 6 | 1 | 1 | 0 | 1 | 1 | 1 |
| 0.4 | 4 | 1 | 1 | 1 | 1 | 1 | 1 |
| 0.1 | 2 | 1 | 1 | 1 | 1 | 1 | 1 |
| 0.0 | 0 | 1 | 1 | 1 | 1 | 1 | 1 |

As shown in the above table, computations were added to the set of battery data to duplicate the existing run-time remaining algorithm that is implemented in the disclosed infusion system. Using this computed run-time remaining value, the times at which the current algorithm would issue the low, very low, and depleted battery alarms were added to the data. This was compared to the ideal time at which those alarms should be issued. The highlighted cells in the table show when the conventional method for generating an alarm, and the disclosed method for generating an alarm would issue the low (30 minute), very low (15 minute), and depleted battery (3 minutes) alarms.

The above table shows that the previous known algorithm used in the infusion system has a significant difference between when it issues the battery alarms versus the ideal pletely). This is 45 minutes of additional run-time on battery that is lost due to the margin that is needed for the previous known algorithm.

As mentioned previously, the times at which the disclosed method utilizing the disclosed neural network model issued the battery alarms correlated very closely to the times issued by an ideal algorithm. Thus, the disclosed approach can be considered to match the ideal case most of the time. Using the neural network can allow a reduction in the run-time remaining margin, and therefore a longer run-time on battery.

Example Infusion System and Infusion Device

Figure 6:
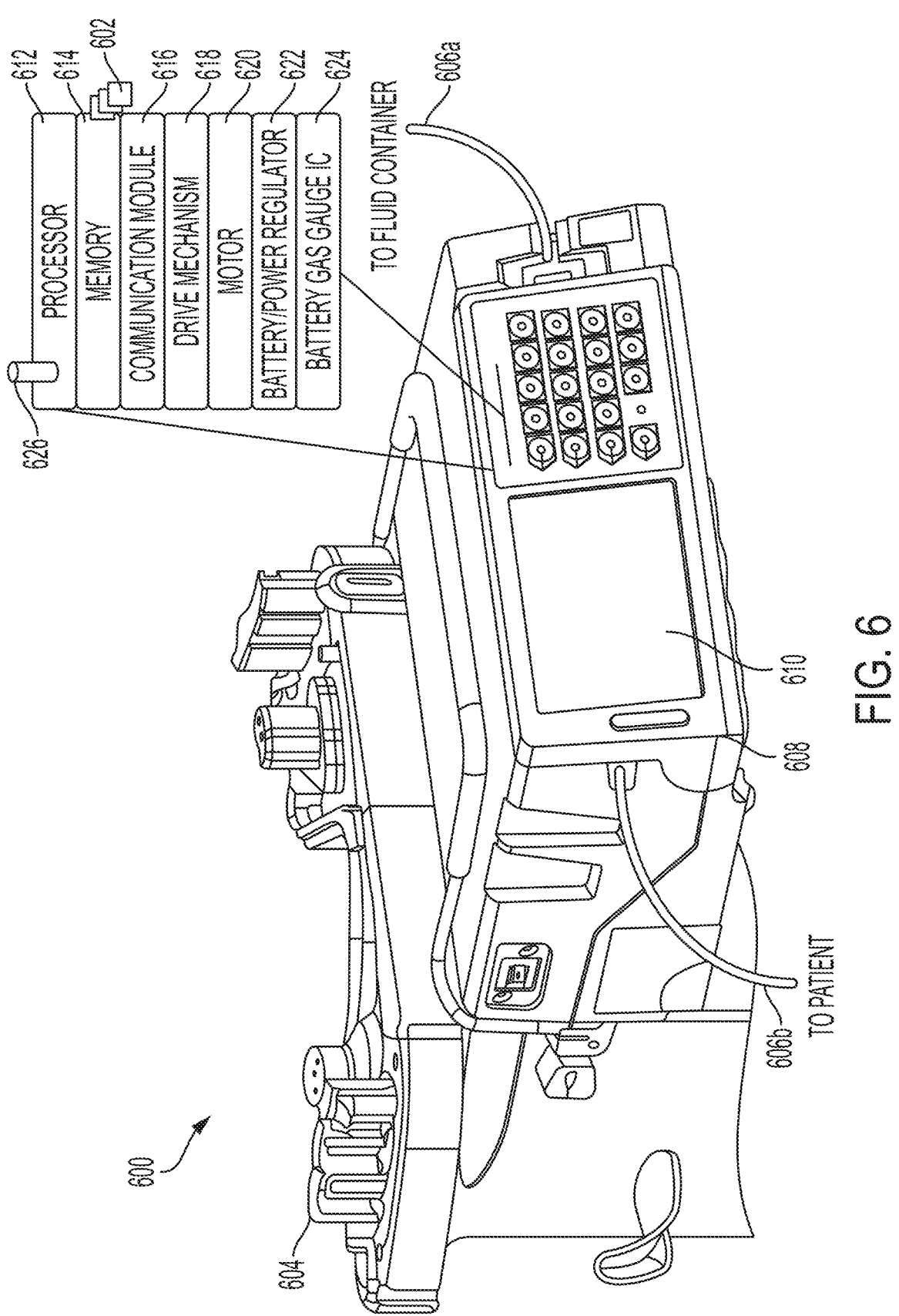
FIG. 6 is a diagram of an infusion device that is configured to use a trained neural network to perform the method of FIG. 5, according to an example embodiment of the present disclosure.

FIG. 6 is a diagram of an infusion device 600 that is configured to use a trained neural network 602 to perform the method of FIG. 5, according to an example embodiment of the present disclosure. The infusion device 600 is an infusion pump, such as a syringe pump, an ambulatory pump, or a peristaltic pump. The infusion device 600 is connected to a rack 604 for support.

The infusion device 600 is configured to receive IV tubing 606. In an example, a cover 608 of the infusion device 600 opens, enabling the IV tubing 606 to be inserted. A first end of the IV tubing 606a is fluidly coupled to a fluid container that holds a drug, medication, or other fluid for an infusion treatment. A second end of the IV tubing 606b is fluidly coupled to a patient via an intravenous connection.

The infusion device 600 includes a user interface 610 for receiving operator inputs (e.g., a flow rate) such as the one or more parameters discussed above. The user interface 610 also displays information including a status of an infusion treatment and alarms/alerts indicative of a low battery including the "low" battery alert, the "very low" battery alert, and the "depleted" battery alert. The user interface 610 includes a touchscreen and a keypad. In other embodiments, the user interface 610 may include only a touchscreen or a keypad.

The infusion device 600 of FIG. 6 also includes a processor 612, a memory 614, and a communication module 616. While one processor 612 is shown, the infusion device 600 may include a plurality of processors. The processor 612 includes a controller, a logic device, etc. configured to execute the trained neural network 602 (e.g., an algorithm) stored in the memory 614. The processor 612 is also configured to execute one or more instructions stored in the memory 614 that, when executed by the processor 612, cause the processor 612 to perform the operations described herein to provide an infusion treatment. The memory 614 includes any memory device including read only memory, flash memory, random access memory, a hard disk drive, a solid state drive, etc.

The communication module 616 is configured for wireless and/or wired communication with a network, such as the Internet, a cellular network, and/or a local hospital network. The communication module 616 may be configured, for example, for Wi-Fi or Ethernet communication. In the illustrated example, the communication module 616 is configured to receive the trained neural network 602 (including weight factors/biases parameters $\omega_{ji}$ and $b_j$) from a server or clinician computer via a network. In other examples, the processor 612 may perform the method of FIG. 5 to train the neural network 602. The communication module 616 may also receive one or more parameters specifying an infusion treatment to be performed. Further, the communication module 616 may transmit alert or alarm messages to a server when a low battery is detected.

The infusion device 600 of FIG. 6 further includes a drive mechanism 618, a motor 620, a battery/power regulator 622, and a battery gas gauge IC 624. Together, the drive mechanism 618 and the motor 620 comprise a pumping mechanism. The processor 612 is configured to transmit signals or commands to the motor 620, which cause the motor 620 to rotate or otherwise operate in a certain direction and speed. The movement or rotation of a drive shaft of the motor 620 causes the drive mechanism 618 to actuate or otherwise provide force on the IV tubing 606 (or a fluid container in alternative embodiments where a fluid container is placed inside the infusion device). The drive mechanism 618 may include finger actuators or a rotary actuator that apply pressure on the IV tubing 606 to deliver fluid from the fluid container to a patient for an infusion treatment. The drive mechanism 618 and the motor 620 are collectively configured to provide precise control of fluid delivery between 0.1 milliliters/hour up to 1000 milliliters/hour.

For a syringe pump, the drive mechanism 618 may include a piston or other actuator that pushes on a plunger of a syringe. In some embodiments, the motor 620 may rotate a drive screw, which causes the drive mechanism 618 to apply force on the plunger.

The battery/power regulator 622 is configured to provide electrical power for the infusion device 600. A power regulator converts outlet based AC power into DC power. A battery provides constant DC power. The battery is rechargeable battery via the AC power. The battery gas gauge IC 624 transmits information regarding the battery 622 to the processor 612. The information may include a type of the battery 622, which is used for selecting the trained neural network 602 from the memory 614. The information also includes remaining voltage/capacity of the battery 622. The information may further include measurements including a voltage of the rechargeable battery, a change in the voltage over the predetermined interval of time, an average current associated with the rechargeable battery, and/or a temperature of the rechargeable battery.

Alternatively, the processor 612 determines or receives in real-time at predetermined intervals of time, measurements including a voltage of the rechargeable battery 622, a change in the voltage over the predetermined interval of time, an average current associated with the rechargeable battery, and/or a temperature of the rechargeable battery. As discussed above in connection with FIG. 5, the processor 612 applies the received information as inputs to the trained neural network 602 and receives an output indicative of a status of the battery 622. Generally, the status indicates that the battery 622 has sufficient charge. However, the trained neural network 602 outputs the low battery, very low battery, or depleted battery status when the inputs are indicative of that battery state. The processor 612 is configured to display an alarm/alert to indicate when the low battery, very low battery, or depleted battery status is present. Further, the processor 612 uses the communication module 616 to transmit the battery alarm/alert to a network.

The processor 612 may include one or more sensors 626 for measuring one or more of a voltage of the rechargeable battery 622, a change in the voltage over the predetermined interval of time, an average current associated with the rechargeable battery, and/or a temperature of the rechargeable battery. In other instances, the sensors 626 are provided in proximity to the battery 622 and communicatively coupled to the processor 612. The sensors 626 may include a voltage meter, a current meter, and/or a temperature gauge. In some instances the voltage meter and the current meter may be integrated with the processor 612 while the temperature gauge is provided in proximity to the battery 622.

In some embodiments, the processor 612 compares the battery status output from the trained neural network 602 to a time remaining for an infusion treatment. If the battery status indicates that the battery will be depleted before the infusion treatment is timed to end, the processor 612 may generate a more pronounced alarm on the user interface 610 and/or for transmission to the network to indicate an infusion treatment will not be adequately completed.

It should be appreciated that the processor 612 performs a battery state determination during infusion treatments and when infusion treatments are not in progress. As such, the trained neural network 602 uses the change in battery voltage over time to assess how quickly the battery 622 is being drained, which corresponds to whether an infusion treatment is being performed. The processor 612 performs the battery state determination at periodic intervals, such as every 50 milliseconds, 100 milliseconds, 500 milliseconds, 1 second, 2 seconds, 5 seconds, 30 seconds, 1 minute, etc.

It should also be appreciated that the depleted battery state corresponds to a battery voltage where the gas gauge IC 624 prevents any further drain from the battery 622. To prevent permanent damage to the battery from a complete drain, the gas gauge IC 624 may prevent further current drain when the battery 622 has at least some charge, such as 0.5 volts or 0.1 volts. In some embodiments, the processor 612 may cause the infusion device 600 to enter a fail-safe mode after the depleted battery state is reached. The fail-safe mode may include a controlled powering down of the infusion device 600.

Figure 7:
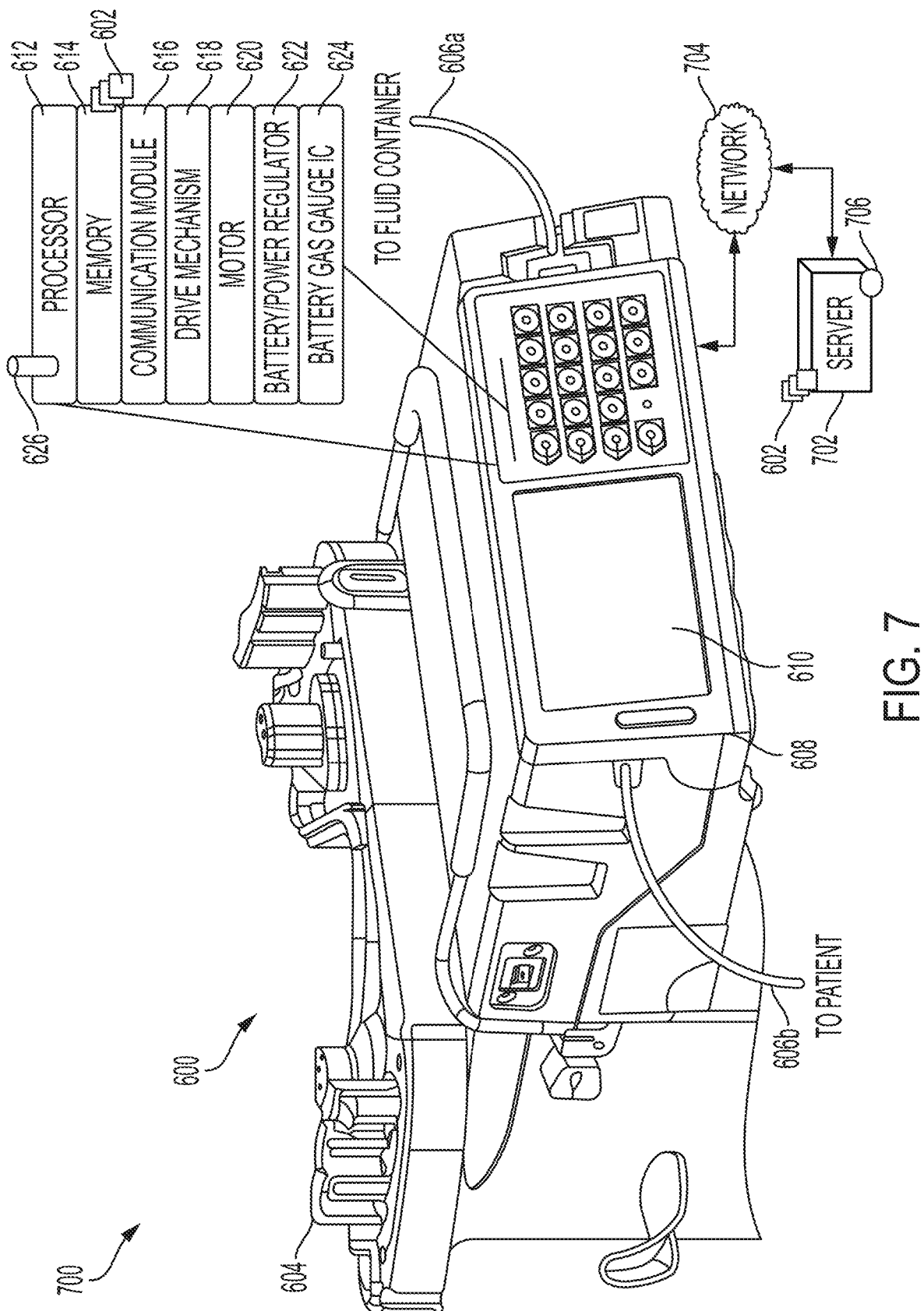
FIG. 7 is a diagram of an infusion system configured to perform the operations described in connection with FIG. 4, according to an example embodiment of the present disclosure.

FIG. 7 is a diagram of an infusion system 700 configured to perform the operations described in connection with FIG. 4, according to an example embodiment of the present disclosure. The infusion system 700 includes the infusion device 600 of FIG. 6. The infusion system 700 also includes a server 702 that is connected to the infusion device 600 via a network 704, which may include any cellular, wide area, and/or local area network. The server 702 may be part of a heath information system and include a clinician computer.

In the illustrated example, the server 702 receives reference training data 706, such as the reference feature vectors discussed above. The training data 706 may be input into the server 702 from manually obtained data. Additionally or alternatively, the training data 706 may be received from one or more infusion devices including the infusion device 600.

As discussed above, the server 702 is configured to create one or more trained neural networks 602 for types of batteries using the training data 706. The server 702 may transmit the trained neural networks 602 to the infusion device 600 via the network 704. Alternatively, the server 702 may receive battery type information from the infusion device 600 (via the gas gauge IC 624) before a treatment is to be begin. The server 702 selects the trained neural network 602 that matches or corresponds to the received battery information and transmits the selected trained neural network 602 (and weight factors/biases parameters $\omega_{ji}$ and $b_j$) to the infusion device 600 for battery state detection.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An infusion device comprising:
  a processor; and
  a memory storing instructions that, when executed by the processor, cause the processor to:
    at least one of receive or determine, at predetermined intervals of time in real-time, measurements comprising at least three of:
    a voltage of a rechargeable battery,
    a change in the voltage over the predetermined intervals of time,
    an average current associated with the rechargeable battery, a temperature of the rechargeable battery, and
    a remaining voltage or capacity of the rechargeable battery,
    generate a feature vector comprising a full charge voltage or capacity of the rechargeable battery in addition to the at least three of the voltage, the change in the voltage, the average current, the temperature, and the remaining voltage or capacity,
    apply the feature vector to a trained neural network to determine an actual remaining voltage or capacity of the rechargeable battery, and
    generate, in real-time, an alarm when the actual remaining voltage or capacity of the rechargeable battery is below at least one of a first threshold corresponding to a low battery state, a second threshold corresponding to a very low battery state, and a third threshold corresponding to a depleted battery state,
    wherein
      when the first threshold is reached and the second threshold is not reached, the processor indicates the low battery state for the alarm,
      when the first and second thresholds are reached and the third threshold is not reached, the processor indicates the very low battery state for the alarm, and
      when the first, second, and third thresholds are reached, the processor indicates the depleted battery state for the alarm.

2. The infusion device of claim 1, wherein the trained neural network comprises weight factors and biases for calculating a plurality of paths through a plurality of layers.

3. The infusion device of claim 1, wherein the processor is configured to display an indication of the alarm on a user interface.

4. The infusion device of claim 1, wherein the processor is configured to transmit the alarm to a server via a network.

5. The infusion device of claim 1, wherein the low battery state corresponds to 30 minutes before the depleted battery state is reached and the very low battery state corresponds to 15 minutes before the depleted battery state is reached.

6. The infusion device of claim 5, wherein the depleted battery state corresponds to three to four minutes before the rechargeable battery is depleted and can no longer provide power.

7. The infusion device of claim 1, wherein the processor is configured to generate feature vectors and apply the feature vectors in real-time to the trained neural network at periodic intervals including at least one of every 50 milliseconds, 100 milliseconds, 500 milliseconds, 1 second, 2 seconds, 5 seconds, 30 seconds, or 1 minute.

8. A medical device comprising:
  a rechargeable battery;
  a user interface;
  a battery sensor;
  a processor communicatively coupled to the battery sensor; and
  a memory storing a plurality of trained neural networks for different rechargeable battery types and instructions that, when executed by the processor, cause the processor to:
    determine, from the rechargeable battery, information indicative of a type of the rechargeable battery,
    select one of the plurality of trained neural networks based on the information indicative of the type of the rechargeable battery, at least one of receive or determine, at predetermined intervals of time in real-time, measurements comprising at least three of:

a voltage of the rechargeable battery from the battery sensor, a change in the voltage over the predetermined intervals of time, an average current associated with the rechargeable battery from the battery sensor, a temperature of the rechargeable battery from the battery sensor, and a remaining voltage or capacity of the rechargeable battery, generate a feature vector comprising a full charge voltage or capacity of the rechargeable battery in addition to the at least three of the voltage, the change in the voltage, the average current, the temperature, and the remaining voltage or capacity, apply the feature vector to the selected trained neural network to determine an actual remaining voltage or capacity of the rechargeable battery, and generate, in real-time, an alarm when the actual remaining voltage or capacity of the rechargeable battery is below at least one of a first threshold corresponding to a low battery state, a second threshold corresponding to a very low battery state, and a third threshold corresponding to a depleted battery state, wherein when the first threshold is reached and the second threshold is not reached, the processor indicates the low battery state for the alarm, when the first and second thresholds are reached and the third threshold is not reached, the processor indicates the very low battery state for the alarm, and when the first, second, and third thresholds are reached, the processor indicates the depleted battery state for the alarm.

9. The medical device of claim 8, wherein the battery sensor includes a plurality of battery sensors, and wherein the voltage of the rechargeable battery is determined by a first battery sensor, the average current associated with the rechargeable battery is determined by a second battery sensor, the temperature of the rechargeable battery is determined by a third battery sensor, and the remaining voltage or capacity of the rechargeable battery is determined by a fourth battery sensor.

10. The medical device of claim 8, wherein the processor is configured to generate feature vectors and apply the feature vectors in real-time to the selected trained neural network at periodic intervals including at least one of every 50 milliseconds, 100 milliseconds, 500 milliseconds, 1 second, 2 seconds, 5 seconds, 30 seconds, or 1 minute.

11. The medical device of claim 8, wherein the trained neural network comprises weight factors and biases for calculating a plurality of paths through a plurality of layers.

12. The medical device of claim 8, wherein the processor is configured to display an indication of the alarm on the user interface.

13. The medical device of claim 8, wherein the medical device is one of a peristaltic pump, a syringe pump, or an ambulatory pump.

14. The medical device of claim 8, wherein at least one of the processor or the rechargeable battery is configured to prevent further current drain of the rechargeable battery when the depleted battery state is reached.

15. The medical device of claim 8, wherein the processor is configured to transmit the alarm to a server via a network.

16. The medical device of claim 15, wherein the processor is configured to:

receive the plurality of trained neural networks for the different rechargeable battery types from the server; and store the plurality of trained neural networks to the memory.

* * * * *